(12) United States Patent
Kong et al.

(10) Patent No.: US 7,146,895 B2
(45) Date of Patent: Dec. 12, 2006

(54) SLIDING BLADE MICROTOME

(76) Inventors: George Y. Kong, 116 Redonovan Dr., Santa Clara, CA (US) 95051; Jian-Qiang Kong, 985-C5 Spring Forest Rd., Greenville, NC (US) 27834

(*) Notice: Subject to any disclaimer, the term of this patent is extended or adjusted under 35 U.S.C. 154(b) by 201 days.

(21) Appl. No.: 10/969,350

(22) Filed: Oct. 21, 2004

(65) Prior Publication Data
US 2006/0086221 A1   Apr. 27, 2006

(51) Int. Cl.
*B26D 1/10* (2006.01)
(52) U.S. Cl. .................... 83/705; 83/409.2; 83/703
(58) Field of Classification Search .............. 83/915.5, 83/703, 409.2, 705, 563, 613, 638
See application file for complete search history.

(56) References Cited

U.S. PATENT DOCUMENTS

| | | | |
|---|---|---|---|
| 4,455,910 A | 6/1984 | Kraft et al. | |
| 4,625,608 A | 12/1986 | Behme et al. | |
| 4,754,675 A | 7/1988 | Segal | |
| 5,148,729 A | 9/1992 | Krumdieck | |
| 5,161,446 A | 11/1992 | Holbl et al. | |
| 5,461,953 A | 10/1995 | McCormick | |
| 5,522,294 A | 6/1996 | Krumdieck | |
| 5,533,342 A | 7/1996 | Gordon | |
| 5,550,033 A | 8/1996 | Krumdieck | |
| 5,713,255 A | 2/1998 | Izvozichikov et al. | |
| 5,740,708 A | 4/1998 | Tabone | |
| 6,209,437 B1 | 4/2001 | Izvozichikov et al. | |
| 6,253,653 B1 | 7/2001 | Walter et al. | |
| 6,598,507 B1 | 7/2003 | Gunther et al. | |
| 6,634,268 B1 | 10/2003 | Guenther et al. | |
| 6,651,538 B1 | 11/2003 | Tamura et al. | |
| 2003/0101858 A1 | 6/2003 | Tamura et al. | |

FOREIGN PATENT DOCUMENTS

| | | |
|---|---|---|
| DE | 31 27 266 A1 | 1/1983 |
| GB | 2 182 786 A | 5/1987 |

*Primary Examiner*—Charles Goodman
(74) *Attorney, Agent, or Firm*—Richard C. Litman

(57) ABSTRACT

The sliding blade microtome is a tissue specimen cutting device including a specimen syringe and an adjustable cutting mechanism for diagonally slicing the specimen. The specimen syringe is a cylindrical shaft having a first end and a second end for holding and supporting a specimen. The first end has a diameter that is smaller than the diameter of the shaft, forming a compressed lip for applying pressure on the specimen prior to slicing by the blade. The pressure used to compress the gelatin and the specimen holds the gelatin and the specimen in a sturdy position to slice the specimen to precision without chatter marks. The specimen is pushed out of the first end of the specimen syringe by a motor mechanism or a manually adjustable micrometer drive.

11 Claims, 4 Drawing Sheets

SLIDING BLADE MICROTOME

BACKGROUND OF THE INVENTION

1. Field of the Invention

The present invention relates to microtomes, more specifically to a sliding blade microtome.

2. Description of the Related Art

Much modern scientific research involves microscopic analysis. Much of today's microscopic analysis requires tissues to be prepared by devices that provide thin specimens, such as microtomes. Many microtomes are specifically designed for preparing specimen for certain types of microscopes. For instance, rotary microtomes cut thin sections of specimen for light microscopy and ultramicrotomes are used to prepare ultrathin sections for light and electron microscopy. Live tissues, such as brain or liver tissues, are prepared by oscillating or vibrating blade microtomes called vibratomes. Vibratomes are currently employed in biomedical studies such as electrophysiology recording, organotypic tissue culture and immunohistochemistry experiments. Though vibratomes have advanced the study of live and fresh tissues, there are disadvantages, such as slow cutting speeds, inconsistent slice thickness, lack of a support for the specimen and the presence of chatter marks on the sliced specimen, that leave the vibratome lacking as a fully efficient microtome. A microtome is desired that will uniformly slice specimen at a specific thickness without imparting chatter marks on the slices. The microtome should not only securely hold, but also steadily support the specimen. Thus, a microtome solving the aforementioned problems is desired.

SUMMARY OF THE INVENTION

The microtome is a tissue specimen-cutting device for producing high quality specimen slices. The device includes a bath, a specimen syringe for holding, supporting and compressing the specimen, and an adjustable cutting mechanism for diagonally slicing the specimen. The cutting mechanism has a linear way guide, a mounting accessory slidingly attached to the linear way guide, and a cross clamp attached to the mounting accessory, a blade holder being adjustably attached to the cross clamp and holding a blade.

The specimen syringe is a cylindrical shaft having a first end and a second end for holding and supporting a specimen. The shaft and the second end have the same diameter. The first end has a diameter that is smaller than the diameter of the shaft and the second end, forming a compressed lip at the first end. A specimen is prepared by gluing it to a first end of a plunger and embedding the specimen in a gelatin, such as low gel point agarose or similar material. The specimen is pushed out of the first end of the specimen syringe by placing pressure on a second end of the plunger using a motor mechanism or a manually adjustable micrometer drive.

Thus, as the specimen is pushed out of the compressed lip at the first end of the specimen syringe, pressure is applied to the specimen and the gelatin. This pressure functions to compress the gelatin and the specimen when they are forced out of the opening of the specimen syringe, thereby clamping and holding the gelatin and the specimen in a sturdy position to slice the specimen to precision without chatter marks.

The blade of the cutting assembly is disposed adjacent the first end of the specimen syringe. A cutting plane is defined along the first end of the specimen syringe. The blade can be angled by rotating the blade holder about the cross clamp to define a cutting angle against the cutting plane.

Ideally the first end and a portion of the syringe shaft are disposed in a bath through a syringe aperture. The syringe aperture is completely submerged under a buffer medium, which is held in the bath. A sealant ring seals the gap between the specimen syringe and the syringe aperture of the bath, thereby preventing the buffer medium from leaking.

A spacer ring surrounds the specimen syringe and works together with a stopper, which is disposed on the syringe, to determine how much of the syringe will be exposed in the bath. The syringe slides into the bath until the stopper abuts the spacer ring and impedes the syringe from moving. The width of the spacer ring, therefore, directly determines how much of the syringe is exposed. A wide spacer ring allows only a small portion of the syringe to extend into the bath, and a narrow spacer ring allows a larger portion of the syringe to extend into the bath. The specimen, as well as the tissue slices cut by the microtome, is disposed in the bath, where the buffer medium not only provides oxygen and nutrition to the specimen, but also lubricates the blade as it cuts the specimen in the bath.

These and other features of the present invention will become readily apparent upon consideration of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
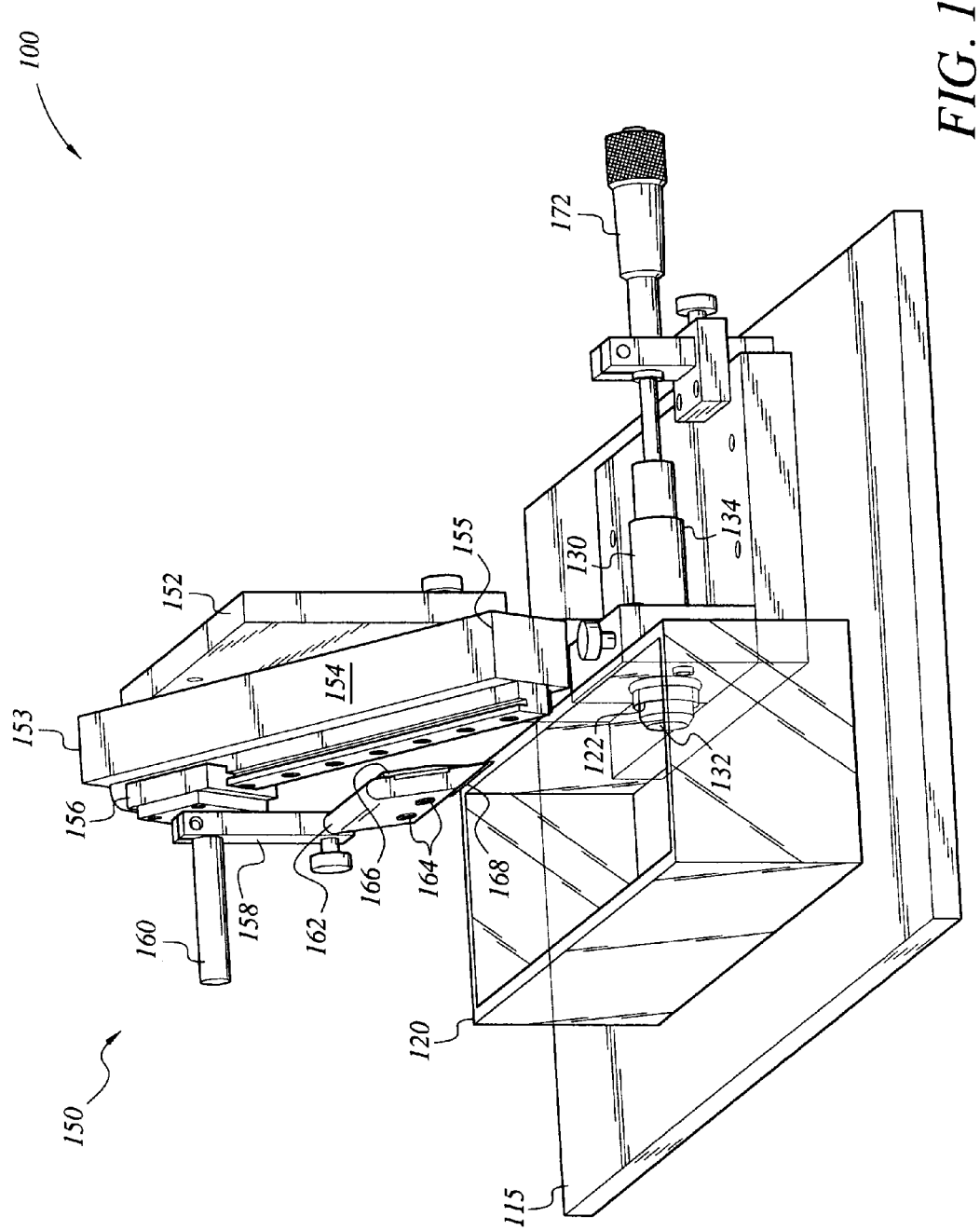
FIG. 1 is an environmental, perspective view of a sliding blade microtome according to the present invention.

The present invention is a sliding blade microtome, a first embodiment of which is designated as 100 in the figures. The sliding blade microtome 100 is a tissue specimen-cutting device for slicing live and pre-fixed tissue. The microtome 100 has a base 115 for supporting a specimen syringe 130 having a first end 132 and a second end 134, a bath 120 having a syringe aperture 122, an adjustable cutting mechanism 150 and a micrometer drive 172. The first end 132 of the specimen syringe 130 is ideally disposed through the syringe aperture 122 of the bath 120. The second end 134 of the syringe 130 is disposed adjacent the micrometer drive 172.

Figure 2:
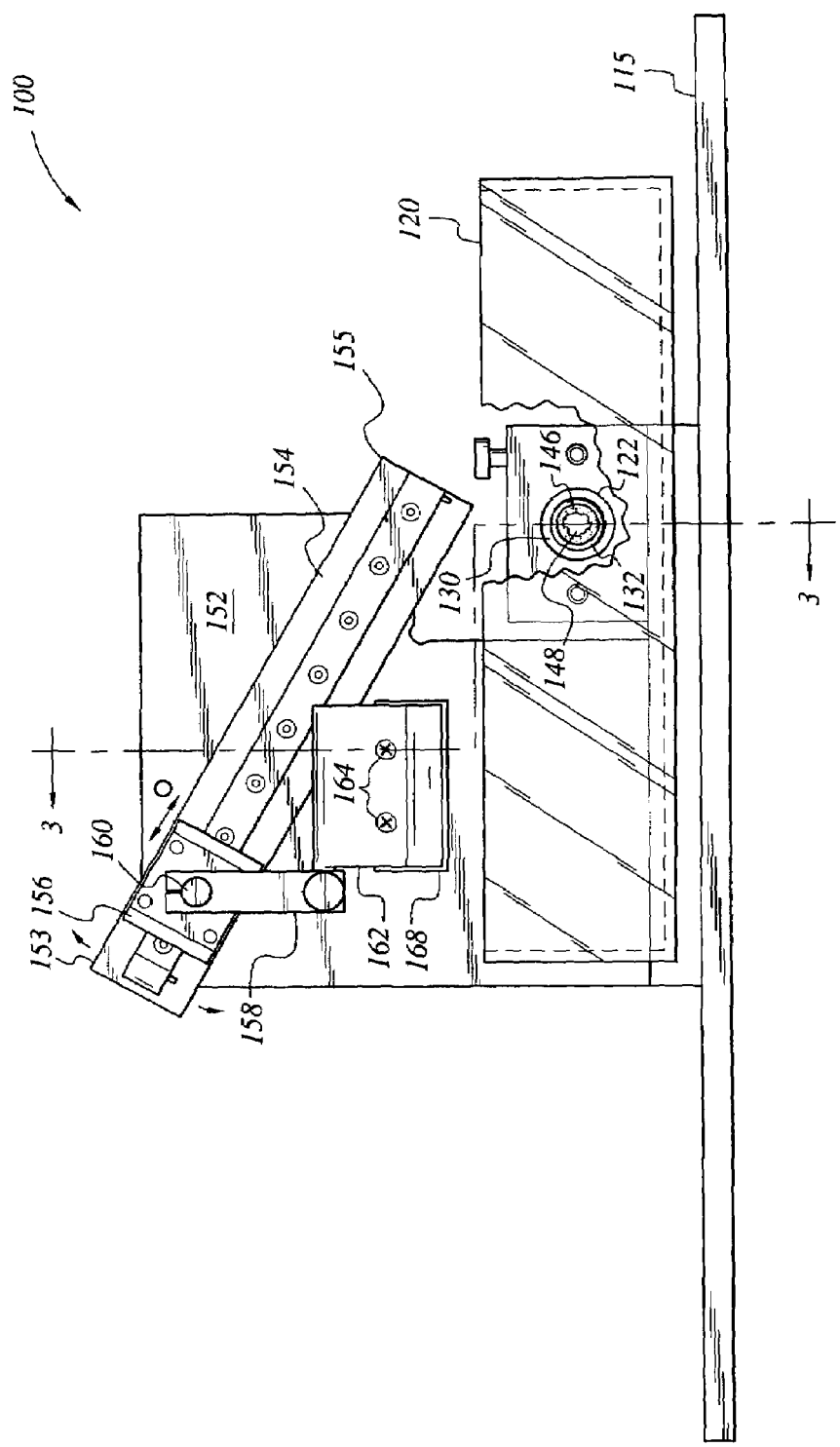
FIG. 2 is a front view of the sliding blade microtome according to the present invention.
Figure 3:
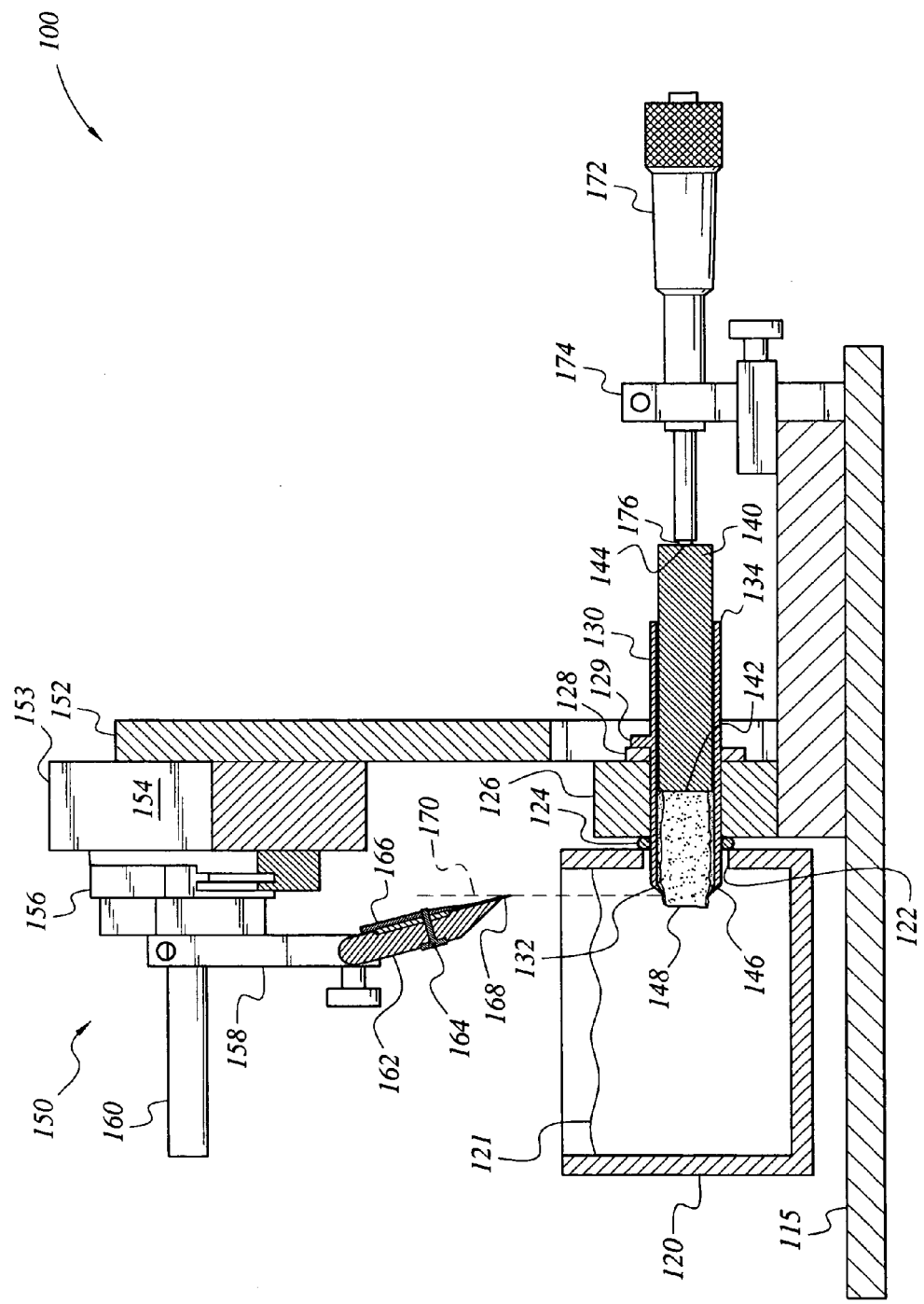
FIG. 3 is a sectional side view of the sliding blade microtome according to the present invention.

Referring to FIGS. 1–3, the cutting mechanism 150 is shown comprising a mounting accessory 156 having an axis rod 160, a cross clamp 158, a blade holder 162 and a blade 168. The cross clamp 158 is disposed on the axis rod 160 of the mounting accessory 156. The cross clamp 158 serves as a support to which the blade holder 162 is pivotally attached. The blade 168 is clamped to the blade holder 162 by a blade clamping plate 166 and is tightened in position using screws 164.

The cutting mechanism 150 is disposed on a linear way guide 154 that is mounted on a support arm 152 of the base 115. The mounting accessory 156 is the portion of the cutting mechanism 150 that directly contacts the guide 154. Specifically, the mounting accessory 156 allows the cutting mechanism 150 to slide from a first end 153 of the linear way guide 154 to a second end 155. The second end 155 of the linear way guide 154 is disposed adjacent the first end 132 of the specimen syringe 130 that is situated within the bath 120. The linear way guide 154 may be tilted up or down to dispose the guide 154 at any angle above the bath 120. The linear way guide 154 is pivoted about a bolt that is secured through one of a number of holes in the support arm 152. The first end 153 of the guide 154 may be level with the second end 155, or may be raised above the second end 155.

Referring now to FIG. 3, the specimen syringe 130 is a cylindrical, hollow shaft designed for supporting and holding a specimen 148. The specimen syringe 130 is positioned and clamped in place on an immovable syringe mount 126 on the base 115. The first end 132 of the syringe 130 has a diameter that is smaller than the diameter of the second end 134 and the body of the syringe 130, and consequentially defines a compressed lip. The compressed lip at the first end 132 has a smaller cross section than the rest of the syringe 130.

The specimen syringe 130 holds the specimen 148 after it is prepared on a plunger 140. The specimen 148 is prepared by being fixed to a first end 142 of the plunger 140 with an adhesive, such as isocyanate glue or the like. Afterwards, the specimen 148 is embedded in a gelatin 146, such as a low gel point agarose, molten agarose or similar material once the specimen 148 is affixed to the plunger 140 in the syringe 130.

The compressed lip at the first end 132 of the syringe 130 is the mechanism through which pressure is placed on the gelatin 146 and the specimen 148 as they exit the syringe 130. The pressure applied by the compressed lip restricts movement of the specimen 148 and the gelatin 146, holds both the gelatin 146 and the specimen 148 in a firm, sturdy position, and mechanically solidifies the two into a firmer mass. The importance of applying pressure to the gelatin 146 and the specimen 148 prior to being cut is to counteract mechanical stresses of the blade 168 as it cuts the specimen 148. Mechanical stress can cause tissue distortion and cell damage of the specimen 148 during slicing. Thus, due to the pressure from the compressed lip of the first end 132, the specimen 148 can be precisely sliced without chatter marks.

Once the gelatin 146 and the specimen 148 are pushed past the compressed lip of the first end 132 of the syringe 130, the operator can slide the blade 168 from the first end 153 to the second end 155 of the linear way guide 154 to cut the specimen 148. The angle of the linear way guide 154 over the first end 132 of the syringe 130 determines how the specimen 148 is cut. If the guide 154 is angled so that the first end 153 is disposed higher than the second end 155, then the blade 168 cuts the specimen 148 diagonally, since the angle of the guide 154 relative to the support 152 is locked while sliding the cutting mechanism 150 along the guide 154.

The blade 168 slides along the guide 154, abutting the first end 132 of the syringe 130. Specifically, the blade 168, via the blade holder 162, is rotated at an angle from a cutting plane 170, which is the outermost end of the first end 132. The blade 168 forms an acute angel with the cutting plane 170. The cutting plane 170 is perpendicular with the axially oriented syringe 130. The cutting angle may be adjusted by rotating the blade holder 162 in the cross clamp 158 to increase or decrease the angle between the blade 168 and the cutting plane 170. Once the blade 168 cuts slices from the specimen 148, they fall into the bath 120.

As described above, the first end 132 and a portion of the shaft of the syringe 130 are disposed through the syringe aperture 122 of the bath 120. The bath 120 has a bottom wall and at least one peripheral wall extending around the bottom wall; the bath holds a buffer medium 121 such as saline. The syringe aperture 122 is completely submerged under the buffer medium 121. To prevent the buffer medium 121 from leaking a sealant ring 124 seals the gap between the specimen syringe 130 and the wall of the bath 120. The sealant ring 124 is disposed adjacent the syringe aperture 122 and is sandwiched between the bath 120 and the syringe mount 126. The buffer medium 121 both lubricates the blade 168 as it cuts the specimen 148 and provides oxygen and nutrition to the specimen 148 and the specimen slices cut by the microtome 100. In alternative embodiments, the bath 120 may be disposed below the syringe 130 to catch the specimen slices that are cut by the microtome 100.

The portion of the syringe 130 that is disposed through the syringe aperture 122 is determined by a stopper 129 that is welded or otherwise disposed on the outside of the syringe 130, and by a spacer ring 128. The spacer ring 128 surrounds the specimen syringe 130 and is sandwiched between the syringe mount 126 and the stopper 129. The syringe 130 moves axially through the syringe aperture 122 until the stopper 129 abuts the spacer ring 128 and stops the syringe 130. The width of the spacer ring 128 is a significant factor in determining how much of the syringe 130 is exposed in the bath 120. For instance, a wide spacer ring 128 allows only a small portion of the syringe 130 to extend into the bath 120. Narrow spacer rings 128 allow a larger portion of the syringe 130 to extend into the bath 120.

The thickness of the slices cut from the specimen 148 may be controlled by the axial movement of the plunger 140 through the specimen syringe 130. The axial movement of the plunger 140 through the specimen syringe 130 may be controlled manually or mechanically. As shown in FIGS. 1–3, the specimen 148 may be pushed out of the first end 132 of the specimen syringe 130 using a micrometer drive 172. A micrometer tip 176 of the micrometer drive 172 is positioned at a second end 144 of the plunger 140 and incrementally pushes the specimen 148 out of the first end 132 of the syringe 130. The micrometer drive 172 is mounted on a micrometer mounting block 174 of the base 115.

Figure 4:
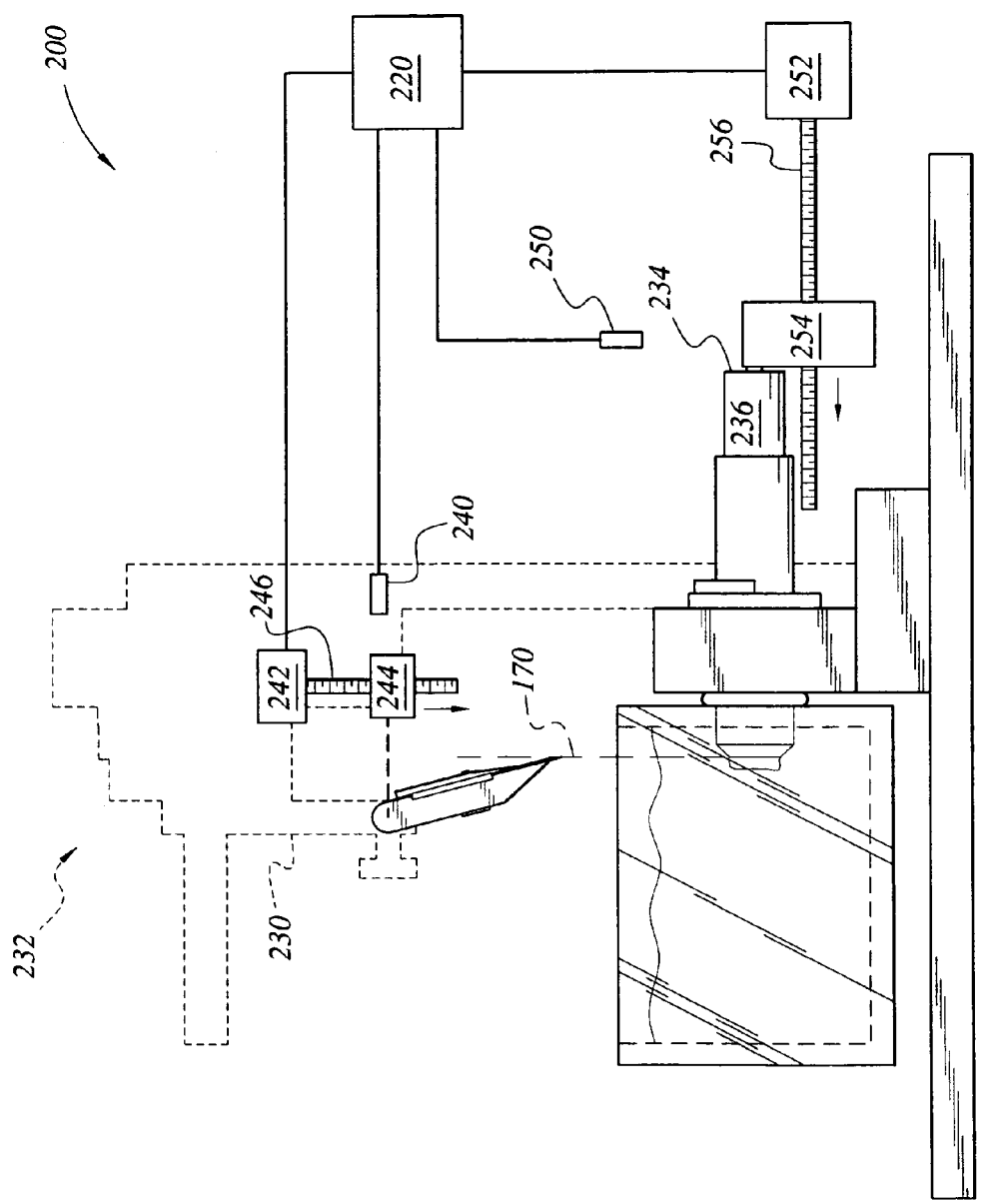
FIG. 4 is a sectional side view of a sliding blade microtome with a mechanical control mechanism according to the present invention.

FIG. 4 shows a second embodiment of the microtome, which is an automated microtome 200 that drives the plunger 236 through the syringe 130 via a control unit 220, sensors 240, 250, motors 242, 252, lead screw blocks 244, 254 and lead screw 246, 256. The motor 242 drives cutting mechanism 232 through lead screw 246 and lead screw block 244. The motor 252 operates the plunger 236, moving it forward using lead screw 256 and lead screw block 254. The control unit 220 monitors the positions of the lead screw blocks 244, 254 through sensors 240, 250, respectively, and sends commands to control the motors 242, 252, respectively.

The microtomes 100, 200 differ in how the plungers 140 and 236, respectively, are pushed out of the syringe 130. However, both microtomes 100, 200 hold and support the specimen 148 using the specimen syringe 130. Also, both have the compressed lip at the first end 132 to compress the specimen 148 prior to being sliced by the blade 168. Furthermore, the cutting mechanism 150, 232 of each microtome 100, 200 is directed to slidingly cut specimen 148 directly within the bath 120 as the blade 168 slides from the first end 153 to the second end 155 of the linear way guide 154.

It is to be understood that the present invention is not limited to the embodiments described above, but encompasses any and all embodiments within the scope of the following claims.

We claim:

1. A microtome, comprising:
   a base;
   a bath disposed on the base, the bath being adapted for holding a buffer medium, the bath having a bottom wall and at least one peripheral wall extending around the bottom wall, the bath having a syringe aperture defined therein;
   a specimen syringe having a hollow shaft extending through the syringe aperture of the bath, wherein the shaft of the syringe has a first end and a second end, the first end extending into the bath, the first end having a constricted diameter forming a lip for compressing the specimen exiting the first end of the syringe;
   a plunger having a first end and a second end, the first end of the plunger forming a holding surface adapted for having a specimen secured thereto, the plunger being slidably disposed in the specimen syringe; and
   a cutting mechanism attached to the base adjacent the first end of the specimen syringe;
   whereby the specimen is pushed through the syringe shaft into the bath and the cutting mechanism slices the specimen within the bath.

2. The microtome of claim 1, wherein the specimen syringe is defined in the peripheral wall of said bath.

3. The microtome of claim 1, wherein the cutting mechanism comprises:
   a linear way guide attached to the base;
   a mounting accessory slidingly attached to the linear way guide;
   a cross clamp attached to the mounting accessory;
   a blade holder attached to the cross clamp; and
   a blade attached to the blade holder.

4. The microtome of claim 3, wherein the linear way guide is pivotally attached to the base.

5. The microtome of claim 3, wherein the blade holder is pivotally attached to the cross clamp.

6. The microtome of claim 3, wherein a cutting plane is defined normal to the first end of the shaft, said blade forming an acute angle with the cutting plane.

7. The microtome of claim 3, wherein the mounting accessory is slidable along the linear way guide to a position in which said blade abuts the first end of the syringe shaft, thereby slicing the specimen into the bath.

8. The microtome of claim 1, further comprising a micrometer drive attached to the base and abutting the second end of the plunger, the micrometer drive impelling the specimen out of the syringe into the bath.

9. A microtome comprising:
   a base;
   a bath disposed on the base, the bath being adapted for holding a buffer medium, the bath having a bottom wall and at least one peripheral wall extending around the bottom wall, the bath having a syringe aperture defined therein;
   a specimen syringe having a hollow shaft extending through the syringe aperture of the bath;
   a plunger having a first end and a second end, the first end of the plunger forming a holding surface adapted for having a specimen secured thereto, the plunger being slidably disposed in the specimen syringe;
   a cutting mechanism attached to the base adjacent the first end of the specimen syringe; and
   a control unit comprising:
      motorized means for sliding the cutting mechanism; and
      motorized means for advancing the plunger in the syringe;
   whereby the specimen is rushed through the syringe shaft into the bath and the cutting mechanism slices the specimen within the bath.

10. A microtome, comprising:
    a base;
    a specimen syringe mounted on the base, the specimen syringe being a hollow shaft having a first end and a second end, the first end having a compressed lip;
    a bath disposed on the base, the bath being adapted for holding a buffer medium, the bath having a bottom wall and at least one peripheral wall extending around the bottom wall, the bath having a syringe aperture defined therein for slidably receiving the specimen syringe;
    a plunger having a first end and a second end, the first end of the plunger being adapted for providing a holding surface to which a specimen is disposed; and
    a cutting mechanism attached to the base and slidable across the first end of the specimen syringe.

11. The microtome of claim 10, wherein the cutting mechanism comprises:
    a linear way guide pivotally attached to the base;
    a mounting accessory slidably attached to the linear way guide;
    a cross clamp attached to the mounting accessory;
    a blade holder adjustably attached to the cross clamp; and
    a blade attached to the blade holder aligned with the compressed lip of the specimen syringe.

* * * * *